US011719667B2

(12) United States Patent
Vellaisamy et al.

(10) Patent No.: US 11,719,667 B2
(45) Date of Patent: Aug. 8, 2023

(54) ELECTROCHEMICAL DETECTOR

(71) Applicant: City University of Hong Kong, Kowloon (HK)

(72) Inventors: A. L. Roy Vellaisamy, Kowloon (HK); Chi Kong Terrence Lau, Kowloon Tong (HK); Lin Oo Saw, Kowloon Tong (HK)

(73) Assignee: City University of Hong Kong, Kowloon (HK)

( * ) Notice: Subject to any disclaimer, the term of this patent is extended or adjusted under 35 U.S.C. 154(b) by 815 days.

(21) Appl. No.: 16/668,194

(22) Filed: Oct. 30, 2019

(65) Prior Publication Data
US 2021/0131995 A1    May 6, 2021

(51) Int. Cl.
| | | |
|---|---|---|
| *G01N 27/31* | (2006.01) | |
| *G01N 33/574* | (2006.01) | |
| *B01L 3/00* | (2006.01) | |

(52) U.S. Cl.
CPC ........ *G01N 27/31* (2013.01); *B01L 3/502707* (2013.01); *G01N 33/57446* (2013.01); *G01N 33/57492* (2013.01)

(58) Field of Classification Search
CPC ......... B01L 3/502707; B01L 3/502715; B01L 1/00; B01L 2300/00; B01L 2400/00; G01N 27/31; G01N 27/30; G01N 27/40; G01N 33/5438; G01N 33/57446; G01N 33/57492; G01N 33/50; G01N 33/53; G01N 33/574

See application file for complete search history.

(56) References Cited

U.S. PATENT DOCUMENTS

| | | | | |
|---|---|---|---|---|
| 2005/0026202 A1* | 2/2005 | Edman | ............. | G01N 33/54353 332/185 |
| 2011/0280766 A1* | 11/2011 | Schwarzkopf | ....... | C12Q 1/6816 422/68.1 |
| 2014/0332407 A1* | 11/2014 | Mai | .................... | G01N 27/3276 204/403.01 |

(Continued)

OTHER PUBLICATIONS

Lin, L.-P.; Song, X.-H.; Chen, Y.; Rong, M.; Zhao, T.; Jiang, Y.; Wang, Y.; Chen, X. One-pot synthesis of highly greenish-yellow fluorescent nitrogen-doped graphene quantum dots for pyrophosphate sensing via competitive coordination with Eu3+ ions. Nanoscale 2015, 7, 15427-15433. [CrossRef] [PubMed].

(Continued)

*Primary Examiner* — Gurpreet Kaur
(74) *Attorney, Agent, or Firm* — Renner Kenner Greive Bobak Taylor & Weber

(57) ABSTRACT

An electrochemical detector includes: a solution chamber and a substance selection structure separating the chamber into individual compartments, wherein the solution chamber is arranged to retain and separate solutions in each of the individual compartments; and a pair of electrodes each connecting the respective individual compartment, wherein the pair of electrodes is arranged to form a conductive path across the electrodes when in contact with the solutions retained in the solution chamber. The substance selection structure is arranged to interact with a target substance in the solution so as to alter an electrical characteristic of the conductive path defined by the pair of electrodes, the solution retained in the individual compartments in the solution chamber and the substance selection structure.

15 Claims, 8 Drawing Sheets

(56) References Cited

U.S. PATENT DOCUMENTS

2019/0232282 A1* 8/2019 Pierson ............... B01L 3/50851

OTHER PUBLICATIONS

Yu, X.; Du, R.; Li, B.; Zhang, Y.; Liu, H.; Qu, J.; An, X. Biomolecule-assisted self-assembly of CdS/MoS2/graphene hollow spheres as high-efficiency photocatalysts for hydrogen evolution without noble metals. Appl. Catal. B Environ. 2016, 182, 504-512. [CrossRef].

Fortgang, P.; Tite, T.; Barnier, V.; Zehani, N.; Maddi, C.; Lagarde, F.; Loir, A.-S.; Jaffrezic-Renault, N.; Donnet, C.; Garrelie, F.; et al. Robust Electrografting on Self-Organized 3D Graphene Electrodes. ACS Appl. Mater. Interfaces 2016, 8, 1424-1433. [CrossRef].

Love, J.C.; Wolfe, D.B.; Haasch, R.; Chabinyc, M.L.; Paul, K.E.; Whitesides, G.M.; Nuzzo, R.G. Formation and Structure of Self-Assembled Monolayers of Alkanethiolates on Palladium. J. Am. Chem. Soc. 2003, 125, 2597-2609. [CrossRef].

Berner, S.; Lidbaum, H.; Ledung, G.; Åhlund, J.; Nilson, K.; Schiessling, J.; Gelius, U.; Bäckvall, J.-E.; Puglia, C.; Oscarsson, S. Electronic and structural studies of immobilized thiol-derivatized cobalt porphyrins on gold surfaces. Appl. Surf. Sci. 2007, 253, 7540-7548. [CrossRef].

Cavalleri, O.; Gonella, G.; Terreni, S.; Vignolo, M.; Floreano, L.; Morgante, A.; Canepa, M.; Rolandi, R. High resolution X-ray photoelectron spectroscopy of I-cysteine self-assembled films. Phys. Chem. Chem. Phys. 2004, 6, 4042-4046. [CrossRef].

Korin, E.; Froumin, N.; Cohen, S. Surface Analysis of Nanocomplexes by X-ray Photoelectron Spectroscopy (XPS). ACS Biomater Sci. Eng. 2017, 3, 882-889. [CrossRef].

Ptasi'nska, S.; Stypczy 'nska, A.; Nixon, T.; Mason, N.J.; Klyachko, D.V.; Sanche, L. X-ray induced damage in DNA monitored by X-ray photoelectron spectroscopy. J. Chem. Phys. 2008, 129, 065102. [CrossRef] [PubMed].

Singh, A.T.; Lantigua, D.; Meka, A.; Taing, S.; Pandher, M.; Camci-Unal, G. Paper-Based Sensors: Emerging Themes and Applications. Sensors 2018, 18, 2838. [CrossRef].

Ratajczak, K.; Stobiecka, M. High-performance modified cellulose paper-based biosensors for medical diagnostics and early cancer screening: A concise review. Carbohydr. Polym. 2020, 229, 115463. [CrossRef] [PubMed].

Cao, L.; Han, G.-C.; Xiao, H.; Chen, Z.; Fang, C. A novel 3D paper-based microfluidic electrochemical glucose biosensor based on GO-TEPA/PB sensitive film. Anal. Chim. Acta 2020, 1096, 34-43. [CrossRef] [PubMed].

Liu, B.; Du, D.; Hua, X.; Yu, X.-Y.; Lin, Y. Paper-Based Electrochemical Biosensors: From Test Strips to Paper-Based Microfluidics. Electroanalysis 2014, 26, 1214-1223. [CrossRef].

International Agency for Research on Cancer, WHO. Latest Global Cancer Data: Cancer Burden Rises to 18.1 Million New Cases and 9.6 Million Cancer Deaths in 2018; Worid Health Organization: Geneva, Switzerland, 2018; pp. 1-3.

Baerheim, A.; Sandvik, H. Effect of ale, garlic, and soured cream on the appetite of leeches. BMJ 1994, 309, 1689. [CrossRef] [PubMed].

Arya, S.K.; Estrela, P. Recent Advances in Enhancement Strategies for Electrochemical ELISA-Based Immunoassays for Cancer Biomarker Detection. Sensors 2018, 18, 2010. [CrossRef] [PubMed].

Pan, Q.; Law, C.O.K.; Yung, M.M.H.; Han, K.C.; Pon, Y.L.; Lau, T.C.K. Novel RNA aptamers targeting gastrointestinal cancer biomarkers CEA, CA50 and CA72-4 with superior affinity and specificity. PLoS One 2018, 13, e0198980. [CrossRef].

Hanash, S.M.; Baik, C.S.; Kallioniemi, O. Emerging molecular biomarkers—blood-based strategies to detect and monitor cancer. Nat. Rev. Clin. Oncol. 2011, 8, 142-150. [CrossRef] [PubMed].

Kumar, S.; Kumar, S.; Srivastava, S.; Yadav, B.K.; Lee, S.H.; Sharma, J.G.; Doval, D.C.; Malhotra, B.D. Reduced graphene oxide modified smart conducting paper for cancer biosensor. Biosens. Bioelectron. 2015, 73, 114-122. [CrossRef].

Lee, H.; Park, J.-E.; Nam, J.-M. Bio-barcode gel assay for microRNA. Nat. Commun. 2014, 5, 3367. [CrossRef].

Kazane, S.A.; Sok, D.; Cho, E.H.; Uson, M.L.; Kuhn, P.; Schultz, P.G.; Smider, V.V. Site-specific DNA-antibody conjugates for specific and sensitive immuno-PCR. Proc. Natl. Acad. Sci. USA 2012, 109, 3731-3736. [CrossRef].

Samanta, A.; Maiti, K.K.; Soh, K.-S.; Liao, X.; Vendrell, M.; Dinish, U.S.; Yun, S.-W.; Bhuvaneswari, R.; Kim, H.; Rautela, S.; et al. Ultrasensitive Near-Infrared Raman Reporters for SERS-Based In Vivo Cancer Detection. Angew. Chem. Int. Ed. 2011, 50, 6089-6092. [CrossRef].

Krishnan, S.; Mani, V.; Wasalathanthri, D.; Kumar, C.V.; Rusling, J.F. Attomolar Detection of a Cancer Biomarker Protein in Serum by Surface Plasmon Resonance Using Superparamagnetic Particle Labels. Angew. Chem. Int. Ed. 2011, 50, 1175-1178. [CrossRef].

De La Rica, R.; Stevens, M.M. Plasmonic ELISA for the ultrasensitive detection of disease biomarkers with the naked eye. Nat. Nanotechnol. 2012, 7, 821-824. [CrossRef].

Li, J.; Li, S.; Yang, C.F. Electrochemical Biosensors for Cancer Biomarker Detection. Electroanalysis 2012, 24, 2213-2229. [CrossRef].

Shahrokhian, S.; Ranjbar, S. Aptamer immobilization on amino-functionalized metal-organic frameworks: An ultrasensitive platform for the electrochemical diagnostic of *Escherichia coli* O157:H7. Analyst 2018, 143, 3191-3201. [CrossRef].

Mittal, S.; Kaur, H.; Gautam, N.; Mantha, A.K. Biosensors for breast cancer diagnosis: A review of bioreceptors, biotransducers and signal amplification strategies. Biosens. Bioelectron. 2017, 88, 217-231 [CrossRef] [PubMed].

Hu, J.; Wang, S.; Wang, L.; Li, F.; Pingguan-Murphy, B.; Lu, T.J.; Xu, F. Advances in paper-based point-of-care diagnostics. Biosens. Bioelectron. 2014, 54, 585-597. [CrossRef] [PubMed].

Martinez, A.W.; Phillips, S.T.; Carrilho, E.; Thomas, S.W.; Sindi, H.; Whitesides, G.M. Simple Telemedicine for Developing Regions: Camera Phones and Paper-Based Microfluidic Devices for Real-Time, Off-Site Diagnosis. Anal. Chem. 2008, 80, 3699-3707. [CrossRef] [PubMed].

Dungchai, W.; Chailapakul, O.; Henry, C.S. Electrochemical Detection for Paper-Based Microfluidics. Anal. Chem. 2009, 81, 5821-5826. [CrossRef].

Zhao, C.; Thuo, M.M.; Liu, X. A microfluidic paper-based electrochemical biosensor array for multiplexed detection of metabolic biomarkers. Sci. Technol. Adv. Mater. 2013, 14, 054402. [CrossRef].

Ge, S.; Zhang, L.; Zhang, Y.; Liu, H.; Huang, J.; Yan, M.; Yu, J. Electrochemical K-562 cells sensor based on origami paper device for point-of-care testing. Talanta 2015, 145, 12-19. [CrossRef].

Zhou, G.; Latchoumanin, O.; Bagdesar, M.; Hebbard, L.; Duan, W.; Liddle, C.; George, J.; Qiao, L. Aptamer-Based Therapeutic Approaches to Target Cancer Stem Cells. Theranostics 2017, 7, 3948-3961. [CrossRef].

Kaur, H.; Bruno, J.G.; Kumar, A.; Sharma, T.K. Aptamers in the Therapeutics and Diagnostics Pipelines. Theranostics 2018, 8, 4016-4032. [CrossRef].

Fu, R.K.; Mei, Y.; Wan, G.; Siu, G.; Chu, P.K.; Huang, Y.; Tian, X.; Yang, S.; Chen, J. Surface composition and surface energy of Teflon treated by metal plasma immersion ion implantation. Surf. Sci. 2004, 573, 426-432. [CrossRef].

Leu, K.; Obermayer, B.; Rajamani, S.; Gerland, U.; Chen, I.A. The prebiotic evolutionary advantage of transferring genetic information from RNA to DNA. Nucleic Acids Res. 2011, 39, 8135-8147. [CrossRef].

Schipor, S.; Vladoiu, S.; Baciu, A.E.; Niculescu, A.M.; Caragheorgheopol, A.; Iancu, I.; Plesa, A.; Popescu, A.I.; Manda, D. A comparative analysis of three methods used for RNA quantitation. Rom. Rep. Phys. 2016, 68, 1078-1088.

Seetharaman, S.; Zivarts, M.; Sudarsan, N.; Breaker, R.R. Immobilized RNA switches for the analysis of complex chemical and biological mixtures. Nat. Biotechnol. 2001, 19, 336-341. [CrossRef].

Li, Z.; Zhang, L.; Mo, H.; Peng, Y.; Zhang, H.; Xu, Z.; Zheng, C.; Lu, Z. Size-fitting effect for hybridization of DNA/mercaptohexanol mixed monolayers on gold. Analyst 2014, 139, 3137-3145. [CrossRef].

Jiang, H.; Materon, E.M.; Sotomayor, M.D.P.T.; Liu, J. Fast assembly of non-thiolated DNA on gold surface at lower pH. J. Colloid Interface Sci. 2013, 411, 92-97. [CrossRef].

(56) References Cited

OTHER PUBLICATIONS

Raveendran, M.; Andrade, A.F.B.; Gonzalez-rodriguez, J. Selective and Sensitive Electrochemical DNA Biosensor for the Detection of Bacillus anthracis. Int. J. Electrochem. Sci. 2016, 11, 763-776.

Walschus, F.L.U. Immobilization of Oligonucleotides for Biochemical Sensing by Self-Assembled Monolayers: Thiol-Organic Bonding on Gold and Silanization on Silica Surfaces. Immobil. DNA Chips I 2005, 260, 37-56.

Mariampillai, A.I.; Cruz, J.P.D.; Suh, J.; Sivapiragasam, A.; Nevins, K.; Hindenburg, A.A. Cancer Antigen 72-4 for the Monitoring of Advanced Tumors of the Gastrointestinal Tract, Lung, Breast and Ovaries. Anticancer Res. 2017, 37, 3649-3656. [CrossRef] [PubMed].

Bhalla, N.; Jolly, P.; Formisano, N.; Estrela, P. Introduction to biosensors. Essays Biochem. 2016, 60, 1-8. [CrossRef] [PubMed].

Jawad, Z.A.R.; Theodorou, I.G.; Jiao, L.R.; Xie, F. Highly Sensitive Plasmonic Detection of the Pancreatic Cancer Biomarker CA 19-9. Sci. Rep. 2017, 7, 14309. [CrossRef].

Keçeci, K.; San, N.; Kaya, D. Nanopore detection of double stranded DNA using a track-etched polycarbonate membrane. Talanta 2015, 144, 268-274. [CrossRef].

Nehra, A.; Chen, W.; Dimitrov, D.S.; Puri, A.; Singh, K.P. Graphene Oxide-Polycarbonate Track-Etched Nanosieve Platform for Sensitive Detection of Human Immunodeficiency Virus Envelope Glycoprotein. ACS Appl. Mater. Interfaces 2017, 9, 32621-32634. [CrossRef] [PubMed].

Huang, H.; Shi, H.; Feng, S.; Chen, W.; Yu, Y.; Lin, D.; Chen, R. Confocal Raman spectroscopic analysis of the cytotoxic response to cisplatin in nasopharyngeal carcinoma cells. Anal. Methods 2012, 5, 260-266. [CrossRef].

Ramos, I.R.M.; Malkin, A.; Lyng, F.M. Current Advances in the Application of Raman Spectroscopy for Molecular Diagnosis of Cervical Cancer. BioMed Res. Int. 2015, 2015, 1-9. [CrossRef] [PubMed].

Çulha, M. Raman spectroscopy for cancer diagnosis: How far have we come? Bioanalysis 2015, 7, 2813-2824. [CrossRef] [PubMed].

Moazzez, B.; O'Brien, S.M.; S., E.F.M. Improved Adhesion of Gold Thin Films Evaporated on Polymer Resin: Applications for Sensing Surfaces and MEMS. Sensors 2013, 13, 7021-7032. [CrossRef].

Meade, A.D.; Lyng, F.M.; Knief, P.; Byrne, H.J. Growth substrate induced functional changes elucidated by FTIR and Raman spectroscopy in in-vitro cultured human keratinocytes. Anal. Bioanal. Chem. 2006, 387, 1717-1728. [CrossRef].

Oliveira, R.N.; Mancini, M.C.; Cabral, F.; De Oliveira, S.; Passos, T.M.; Quilty, B. FTIR analysis and quantification of phenols and flavonoids of five commercially available plants extracts used in wound healing. Matéria 2016, 21, 767-779. [CrossRef].

Wood, B.R. The importance of hydration and DNA conformation in interpreting infrared spectra of cells and tissues. Chem. Soc. Rev. 2016, 45, 1980-1998. [CrossRef].

Gallagher, W. FTIR analysis of protein structure. Course Man. Chem. 2009, 455, 1-8.

Joshi, H.C.; Singh, K.P.; Tomar, A.; Singh, P. Application of Nanopore of Solid Membrane for Recognition of fluorescent Pseudomonas. Int. J. Biochem. Biophys. 2017, 5, 53-64. [CrossRef].

Carrascosa, L.G.; Gómez-Montes, S.; Aviñó, A.; Nadal, A.; Pla, M.; Eritja, R.; Lechuga, L.M. Sensitive and label-free biosensing of RNA with predicted secondary structures by a triplex affinity capture method. Nucleic Acids Res. 2012, 40, e56. [CrossRef] [PubMed].

Lee, C.; Gong, P.; Harbers, G.M.; Grainger, D.W.; Castner, D.G.; Gamble, L.J. Surface Coverage and Structure of Mixed DNA/Alkylthiol Monolayers on Gold: Characterization by XPS, NEXAFS, and Fluorescence Intensity Measurements. Anal. Chem. 2006, 78, 3316-3325. [CrossRef].

Mazzotta, E.; Rella, S.; Turco, A.; Malitesta, C. XPS in development of chemical sensors. RSC Adv. 2015, 5, 83164-83186. [CrossRef].

Rosenthal, D.; Ruta, M.; Schlogl, R.; Kiwi-Minsker, L. Combined XPS and TPD study of oxygen-functionalized carbon nanofibers grown on sintered metal fibers. Carbon 2010, 48, 1835-1843. [CrossRef].

Xu, M.; He, G.; Li, Z.; He, F.; Gao, F.; Su, Y.; Zhang, L.; Yang, Z.; Zhang, Y. A green heterogeneous synthesis of N-Toped carbon dots and their photoluminescence applications in solid and aqueous states. Nanoscale 2014, 6, 10307-10315. [CrossRef].

Gammon, W.J.; Kraft, O.; Reilly, A.C.; Holloway, B.C. Experimental comparison of N(1s) X-ray photoelectron spectroscopy binding energies of hard and elastic amorphous carbon nitride films with reference organic compounds. Carbon N. Y. 2003, 41, 1917-1923. [CrossRef].

Wahid, M.; Parte, G.; Phase, D.; Ogale, S. Yogurt: A novel precursor for heavily nitrogen doped supercapacitor carbon. J. Mater. Chem. A 2014, 3, 1208-1215. [CrossRef].

\* cited by examiner

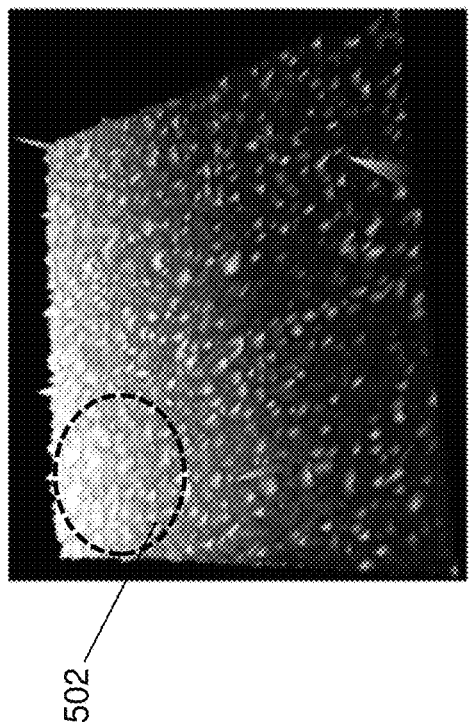 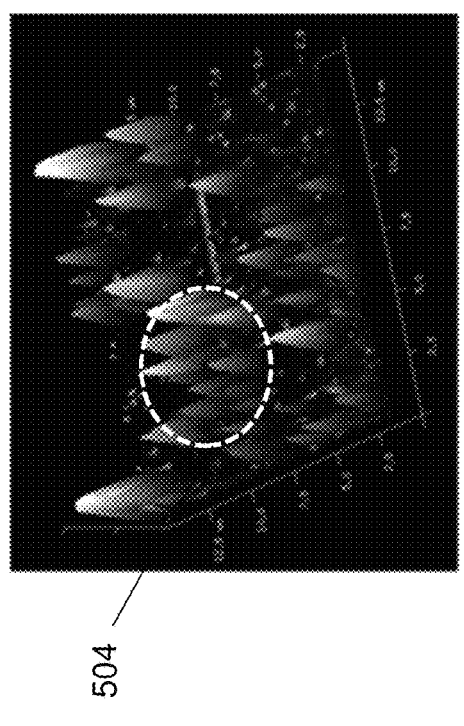

ELECTROCHEMICAL DETECTOR

TECHNICAL FIELD

The present invention relates to an electrochemical detector, specifically, although not exclusively, to an electrochemical detector for detecting biomarkers in a biological sample.

BACKGROUND

A disease is any condition that impairs the normal functioning of the body, which can be generally divided into infectious and non-infectious. Importantly, any improper or delay treatment of a disease could lead to a fatal consequence to a patient, regardless of what type of the disease is. Thus, the screening and diagnosis of the disease is of paramount importance.

Traditional screening methods usually include invasive procedures during sampling process. The screening methods are also time-consuming and require tedious instruments installed in laboratories for carrying out the measurements. Although the results generated therefrom may be very accurate and sensitive, such methods may not be suitable for daily applications which require point-of-care and low-cost setup.

SUMMARY OF THE INVENTION

In accordance with the first aspect of the present invention, there is provided an electrochemical detector comprising: a solution chamber and a substance selection structure separating the chamber into individual compartments, the solution chamber is arranged to retain and separate solutions in each of the individual compartments; and a pair of electrodes each connecting the respective individual compartment, wherein the pair of electrodes is arranged to form a conductive path across the electrodes when in contact with the solutions retained in the solution chamber; wherein the substance selection structure is arranged to interact with a target substance in the solution so as to alter an electrical characteristic of the conductive path defined by the pair of electrodes, the solution retained in the individual compartments in the solution chamber and the substance selection structure.

In an embodiment of the first aspect, the substance selection structure includes a porous layer arranged to capture the target substance.

In an embodiment of the first aspect, the porous layer includes a plurality of receptors arranged thereon, the plurality of receptors are arranged to bind with the target substance.

In an embodiment of the first aspect, the porous layer further includes a coupling agent arranged to couple the plurality of receptors with the porous layer.

In an embodiment of the first aspect, the coupling agent includes a hydroxyl group forming a covalent bond with the plurality of receptors.

In an embodiment of the first aspect, the coupling agent further includes a sulfhydryl group arranged to couple with the porous layer.

In an embodiment of the first aspect, the sulfhydryl group of the coupling agent forms a gold-sulphur bond with the porous layer.

In an embodiment of the first aspect, the coupling agent is 6-mercapto-1-hexanol.

In an embodiment of the first aspect, the plurality of receptors is specific to the target substance, forming a physical interaction with the target substance.

In an embodiment of the first aspect, the plurality of receptors includes a plurality of oligonucleotides forming at least one of electrostatic interactions, hydrophobic interactions or a complementary shape with the target substance.

In an embodiment of the first aspect, formation of the physical interaction decreases a current flow of the conductive path.

In an embodiment of the first aspect, the target substance is a cancer biomarker.

In an embodiment of the first aspect, the cancer biomarker is an antigen of gastric cancer.

In an embodiment of the first aspect, the porous layer is a gold deposited track-etched polycarbonate membrane or a gold deposited porous aluminum membrane.

In an embodiment of the first aspect, the solution chamber is an enclosed chamber.

In an embodiment of the first aspect, the enclosed chamber includes a first portion and a second portion detachably connecting with each other.

In an embodiment of the first aspect, each of the first and the second portions includes an inlet, each connecting to the respective compartments of the chamber, for directing the solutions into the compartments.

In an embodiment of the first aspect, the enclosed chamber further includes an O-ring disposed between the compartments of the first and the second portions, thereby preventing solution leakage from the respective compartments.

In an embodiment of the first aspect, the O-ring is arranged on a side opposite to where the substance selection structure interacts with the target substance.

In an embodiment of the first aspect, the deposited gold has a thickness of about 10 nm.

In an embodiment of the first aspect, the porous layer has a pore size of about 50 nm.

In an embodiment of the first aspect, the porous layer has a thickness of about 7 μm.

BRIEF DESCRIPTION OF THE DRAWINGS

Embodiments of the present invention will now be described, by way of example, with reference to the accompanying drawings in which:

FIG. 5A is an atomic force microscope (AFM) image of the track-etched PC membrane coated with a gold nano-layer;

FIG. 5B is an AFM image of the gold-coated PC membrane of FIG. 5A functionalized with oligo-RNA successfully capturing an antigen of gastric cancer CA72-4;

DETAILED DESCRIPTION

Cancer is one of the mortal diseases in the world and its early detection is essential to improve successful treatment and reduce cancer mortality. Fortunately, long term survival is possible if patients present at an early stage. Thus, diagnostic tools enabling the screening test of cancer become of paramount importance.

In view of the above, it may be desirable to have a low cost cancer screening in the asymptomatic general population. However, it is appreciated that many of the screening methods/devices used in the art require invasive sample collection or time-consuming analysis, whilst both of which may further require a trained person to operate.

The inventors have, through their own research, trials and experiments, devised that aptamers (i.e. RNA or DNA oligonucleotides or peptides) possess structural domains that are capable of recognizing a wide variety of targets such as ions, toxins, bacteria, viruses, cells, and tissues with high selectivity and sensitivity. In addition, the aptamers can be functionalized on different material easily. Thus, an electrochemical detector containing said aptamers may be desirable to provide a low cost, highly selective, and highly sensitive cancer screening.

Figure 1:
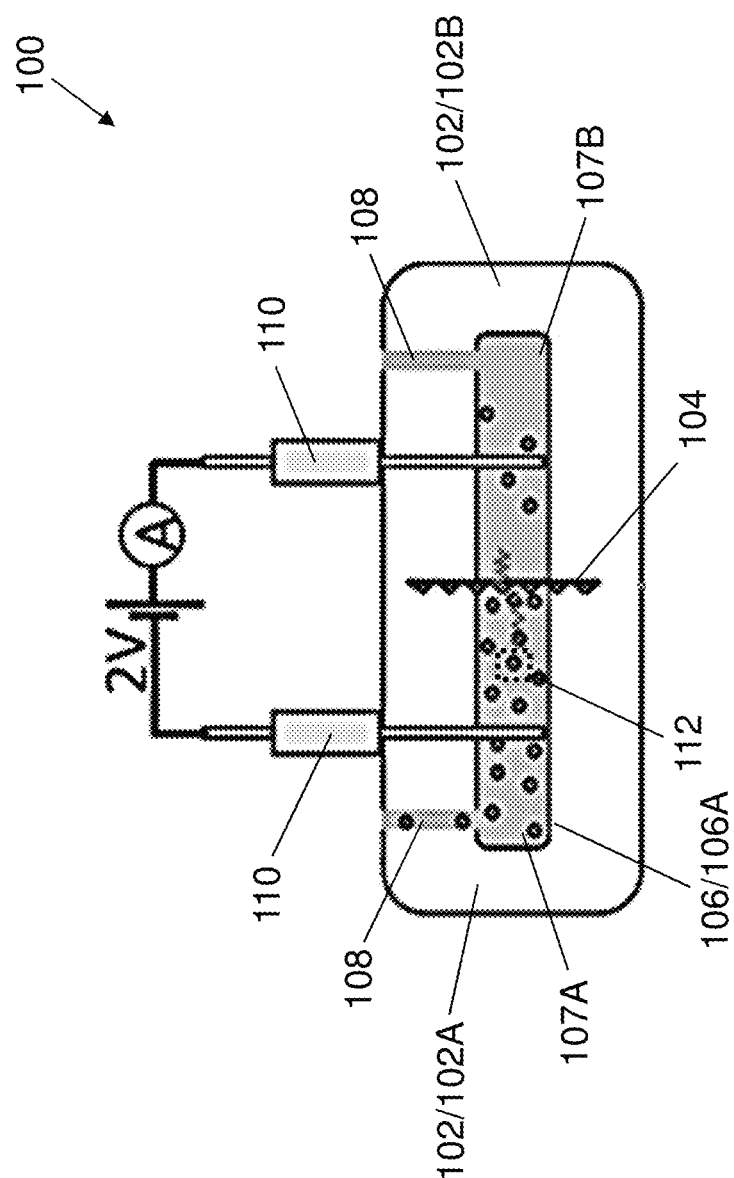
FIG. 1 is a schematic diagram showing an electrochemical detector for detecting a target substance in a sample solution in accordance with one embodiment of the present invention.

With reference to FIG. 1, there is provided an embodiment of an electrochemical detector comprising a solution chamber and a substance selection structure separating the chamber into individual compartments, the solution chamber is arranged to retain and separate solutions in each of the individual compartments; and a pair of electrodes each connecting the respective individual compartment, wherein the pair of electrodes is arranged to form a conductive path across the electrodes when in contact with the solutions retained in the solution chamber; wherein the substance selection structure is arranged to interact with a target substance in the solution so as to alter an electrical characteristic of the conductive path defined by the pair of electrodes, the solution retained in the individual compartments in the solution chamber and the substance selection structure.

In this embodiment, the electrochemical detector 100 may be used for detecting a cancer biomarker in a sample. The electrochemical detector includes a chamber 102. The chamber may be made of any suitable materials or of any shapes. In one example, the chamber may be a unity PVC chamber moulded into a cylindrical shape. In another example, the chamber may include a first portion and a second portion that are detachably connecting with each other. The first and the second portions may have the same shape connected by external means to form an enclosed chamber; or the two portions may have a complementary shape such that they are connected with each other without an external means.

The chamber 102 may also be of any suitable size that can fit a particular use. Preferably, the chamber may have a compact size such that a user may carry the detector 100 around easily and may be able to perform "point-to-point" screening. For example, the chamber may have a length of about 50-60 mm with a height/diameter of about 50 mm. That is, the chamber size may be comparable to a human palm.

The chamber 102 may be petitioned by a substance selection structure 104 into two individual compartments 106A and 106B for retaining solutions 107A and 107B, respectively. Each of the compartments may include an inlet 108 connecting to the respective compartments for directing solutions thereinto. The detector 100 may also include a pair of electrodes 110 inserted into the compartments 106A and 106B, contacting with the solutions retained in the compartments. The electrodes 110 are electrically connected to an external circuit thereby forming a conductive path defined by the electrodes, the solutions retained in the individual compartments, and the substance selection structure.

The substance selection structure 104 may selectively interact with a target substance 112 in the solutions. Upon interaction, one or more molecules of the target substance may be captured by the substance selection structure, rendering a reduction of quantity of the target substance in the solution. As a result, the electrical characteristic of the conductive path is altered. Thus, the presence and/or the amount of the cancer biomarkers in a sample may be indicated based on the electrical characteristic altered by the interaction.

The substance selection structure 104 may include a plurality of receptors arranged to bind with the target substance 112 that are in contact with the substance selection structure. Preferably, the plurality of receptors is specific to the target substance, forming a physical interaction with the target substance upon contact, thereby capturing the target substance. For example, the plurality of receptors may form at least one of electrostatic interactions, hydrophobic interactions, or a complementary shape with the target substance upon contact.

The plurality of receptors may be arranged on a porous layer. The porous layer may act as a support or a substrate allowing the receptors to accommodate thereon. The porous layer may be of any size that allows it to be fitted into the solution chamber 102. Preferably, the porous layer may be a polymeric layer or a metallic layer with nanopores. The nanopores may be introduced to the polymeric layer or metallic layer by reported techniques such as track-etching, ion bean sculpting, electron beam sculpting and the like. Advantageously, with the presence of the nanopores, the porous layer provides a large surface area for accommodating a large amount of receptors, which may increase the chance of the target substance being captured by the receptors, thereby enhancing the sensitivity of the detector.

In one example, the plurality of receptors may be arranged on the porous layer by chemical functionalization of the porous layer. The porous layer may be modified with a layer of active material, which allows seeding a plurality of coupling agents thereon. The coupling agent may have one or more functional groups that can form at least one covalent bond with the receptors and the porous layer, thereby anchoring the receptors onto the porous layer. For example, the coupling agent may have at least one of a hydroxyl group, a sulfhydryl group, an amino group, a siloxane group or a carboxyl group forming at least one covalent bond with the receptors and the porous layer. Detailed structural arrangement of the substance selection structure will be discussed in later part of this disclosure.

In operation, the electrochemical detector 100 may be implemented as a solution chamber 102 including a first portion 102A and a second portion 102B. The first and the second portions may be detachably connecting with each other to form an enclosed chamber 102. The first and the second portions may be connected with each other by any suitable external means. For example, the two portions may be connected with each other by screwing them together with a plurality of screws.

The enclosed chamber 102 may include a compartment 106 for retaining solutions. The compartment is separated by the substance selection structure 104 disposed between the first and the second portions of the chamber, such that the compartment 106 is petitioned into two individual compartments 106A and 106B for retaining different solutions.

Optionally or additionally, an O-ring (not shown) may be disposed opposite to a side where the substance selection structure 104 interacts with the target substance 112 for preventing any solution leaking from the respective compartments.

To perform measurement, the electrochemical detector 100 is connected to an external circuit through the electrodes 110. The electrodes may be made of any conductive materials that are not reactive to the target substance 112. Preferably, the electrodes are made of noble metal such as platinum, gold and the like.

A sample solution containing the target substance 112 and a reference solution may be added to the compartments 106A and 106B, respectively. The solutions may be added to the compartments with a predetermined volume. Preferably, the volume added to the compartments may be minimal, such as 1-2 mL. Depending on how the front side of the substance selection structure 104 is oriented (i.e. whether the side with the plurality of receptors is oriented towards the left or right end of the detector), the sample solution may be added to the compartment 106A or 106B through the inlets 108. In this example, the plurality of receptors is oriented towards the left end of the detector and therefore the sample solution 107A is added to the compartment 106A whereas the reference 107B is added to the compartment 106B.

The target substance 112 in the sample solution 107A may by captured by the substance selection structure 104 when they are in contact. Thus, the amount of target substance in the sample solution is reduced, rendering a reduction of conductivity of the sample solution 107A with respect to the reference solution 107B. As such, the current flow across the electrodes is reduced accordingly. By measuring such alteration in current over time (i.e. current flow), the amount of target substance in the sample solution may be determined.

Figure 2:
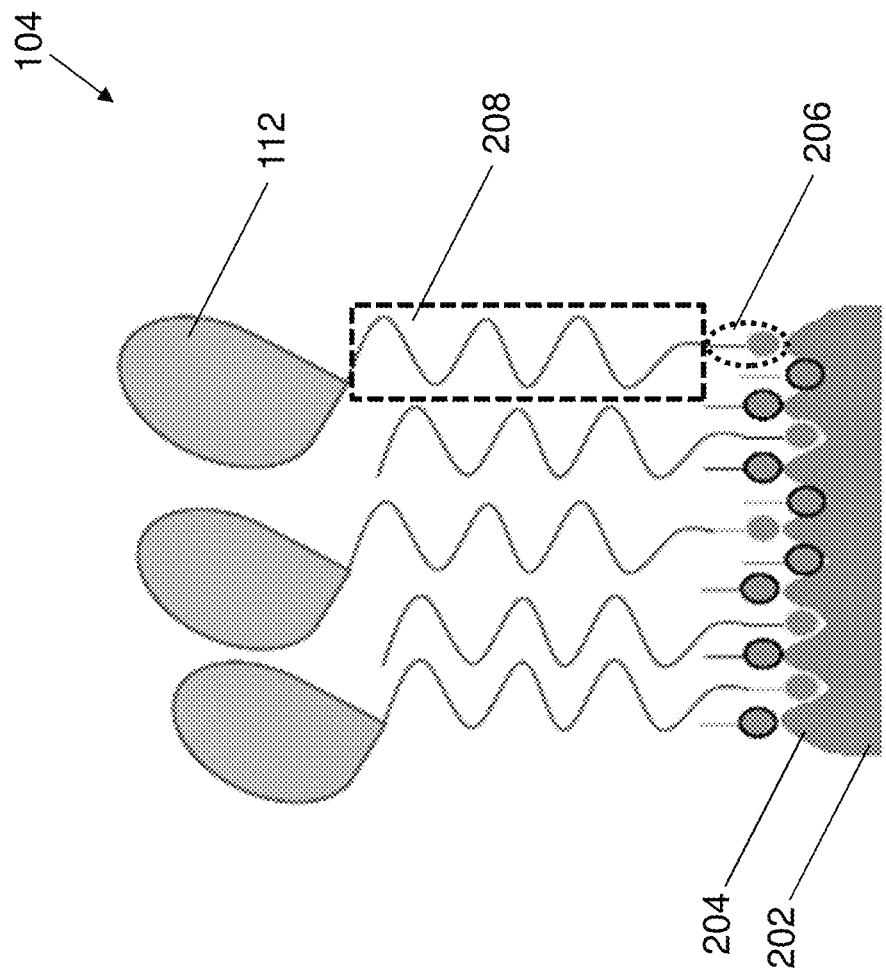
FIG. 2 is a schematic diagram showing a substance selection structure and its interaction with the target substance in accordance with one embodiment of the present invention.
Figure 3A:
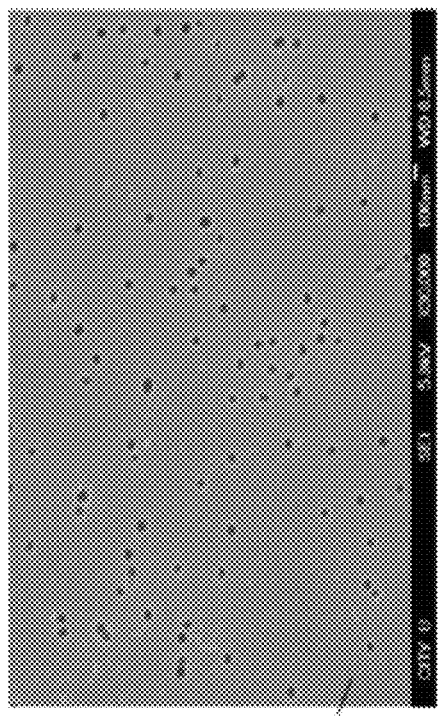
FIG. 3A is a scanning electron microscope (SEM) image of a track-etched polycarbonate (PC) membrane.
Figure 3B:
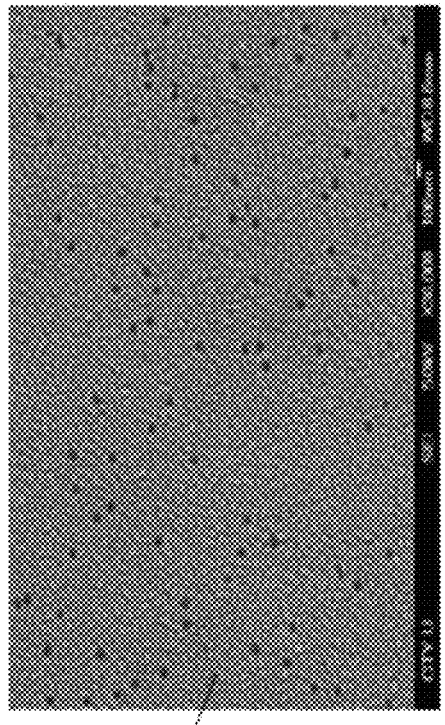
FIG. 3B is a SEM image of the track-etched PC membrane coated with a gold nano-layer.

With reference to FIGS. 2, 3A and 3B, there is provided an exemplary embodiment of the substance selection structure 104. The substance selection structure comprises a porous layer 202 deposited with an active layer 204. The active layer 204 is seeded with a plurality of coupling agents 206. A plurality of receptors 208 are arranged to couple with the coupling agents 206 and are arranged to interact with a target substance 112.

In this example, the porous layer 202 may be a polycarbonate (PC) membrane or an aluminium membrane with a plurality of nanopores. The membrane 202 may have a morphology as shown in FIG. 3A. As shown, the nanopores are distributed non-uniformly on a smooth membrane surface. The membrane 202 may have a thickness of about 7 μm and its pores may have a pore size of about 50 nm. It is appreciated that a skilled person may vary the thickness and pore size of the membrane according to their needs.

The membrane 202 is deposited with the active layer 204. The active layer 204 may act as a platform to seed/to accommodate the coupling agent 206. The active layer 204 may comprise any material that is capable of reacting with at least one of the functional groups of the coupling agent 206. Preferably, the active layer 204 is a gold nano-layer. The gold nano-layer 204 may be deposited on the membrane 202 by reported methods such as spin coating, vapor deposition, dip coating and the like. In this example, the gold nano-layer 204 may have a thickness of about 10 nm. As shown in FIG. 3B, after deposited with the gold nano-layer, the smooth porous membrane 202 is covered with a layer of gold nanoparticles, forming a rough layer thereon.

As mentioned, the coupling agents 206 are arranged to couple the receptors with the membrane 202. In this example, the coupling agent may be an alkyl compound including at least one functional group that is capable of coupling with the receptors 208 and the active layer 204. The alkyl compound may have a carbon chain of 4 to 6 carbons with the functional groups arranged on each end of the carbon chain. The functional groups may be identical or different from each other. Preferably, the coupling agent includes an alkyl compound having a 6C carbon chain with different functional groups arranged on each end of the carbon chain. More preferably, the 6C alkyl compound includes a hydroxyl group and a sulfhydryl group on each end of the compound. Most preferably, the coupling agent is 6-mercapto-1-hexanol (MCH).

The MCH 206 on the one hand may form a gold-sulphur bond with the gold nano-layer 204 through the sulfhydryl group thereby allowing itself to accommodate on the membrane 202. On the other hand, the MCH 206 may form a covalent bond with the receptors 208 through the hydroxyl group such that the receptors are bridged/anchored to the membrane 202.

The receptors 208 may be any compounds with a functional group that can specifically bind to the target substance 112; or any biological molecules that can specifically interact with/capture the target substance 112. In particular, the receptors 208 may be a biological molecule that is specific to a biomarker of a cancer such as an antigen of a particular cancer. In this example, the biological molecule 208 may be an aptamer (i.e. an oligo-RNA/DNA or a peptide) that can specifically capture an antigen of a cancer 112. Preferably, the biological molecule 208 is an oligo-RNA containing a sequence that is specific to the antigen of gastric cancer. The oligo-RNA 208 may form a physical interaction with the antigen 112 when they are in close proximity or in contact with each other. Preferably, the oligo-RNA 208 may form at least one of the electrostatic interactions, hydrophobic interactions or a complementary shape with the antigen 112. By this capturing process, the amount of the antigen in the sample solution would be reduced, thereby altering the conductivity of the sample solution and the amount of current flow from the sample solution to the reference solution in the electrochemical detector 100.

Without being limited by the above example, it is appreciated that the substance selection structure 104 may be applied to capture other cancer biomarkers so as to detect different types of cancer. This may be done by simply replacing the receptors 208 with other aptamers that is specific to the antigen of the cancer of interest.

The use of a coupling agent may be advantageous in facilitating the coupling of the receptors to the membrane. For example, in some cases, the receptors may not have a functional group that is reactive enough to react with the active layer; thereby a harsh reaction condition may be required to anchor/immobilize the receptors on the membrane. Such a harsh reaction condition may cause deterioration to the receptors, particularly when the receptors are nucleotides or peptides, rendering a reduction or a loss of function of the receptors.

By the use of a coupling agent with functional groups that are reactive toward both the receptors and the membrane, the reaction condition required would become milder, increasing the chance of preserving the functionality of the receptors. In addition, the coupling agent may prevent cross-linking between adjacent receptors, particularly when the receptors are aptamers (i.e. oligo-RNA, oligo-DNA or peptides). Thus, the binding between the receptors and the target substance would not be hindered by said cross-linking.

Figure 4:
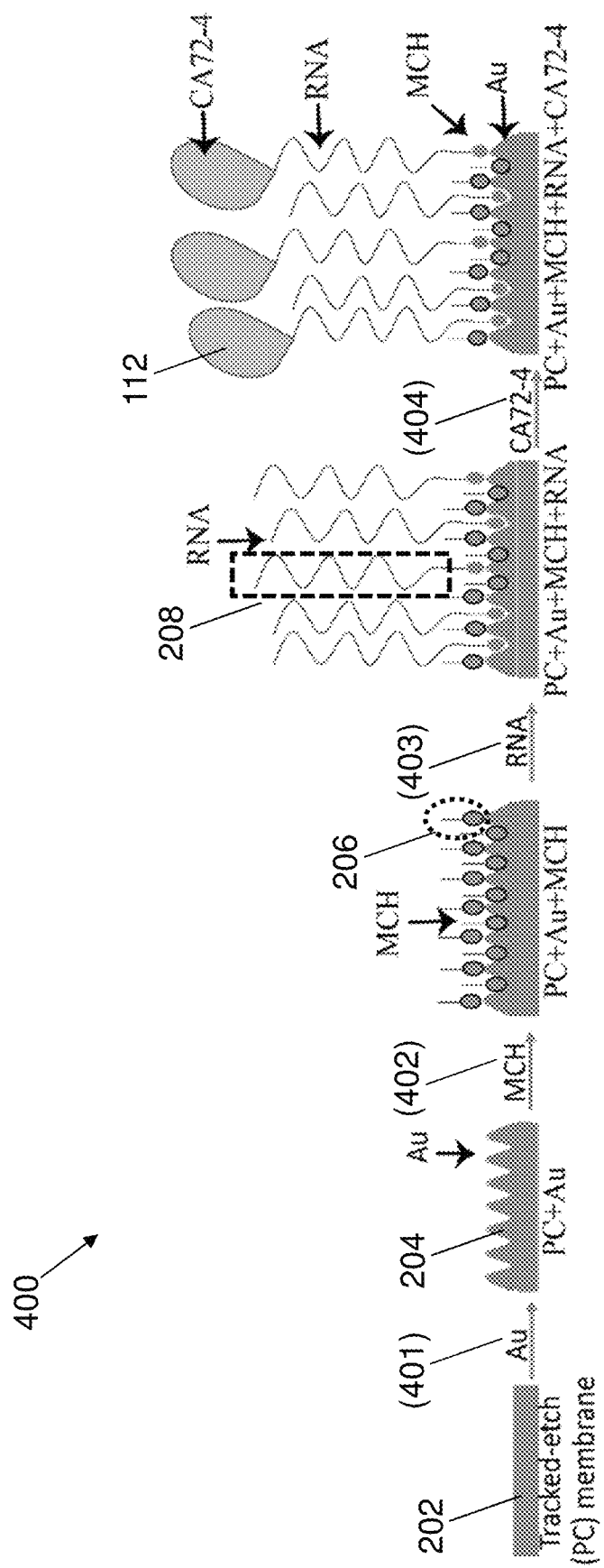
FIG. 4 is a schematic diagram showing a process flow of fabrication of the substance selection structure of FIG. 2.

With reference to FIG. 4, there is shown a method of fabrication of the substance selection structure 104. The method 400 comprises three main steps. The method may commence at step 401 where a porous layer 202 is deposited with a layer of active material 204. In this example, the porous layer is a track-etched polycarbonate (PC) membrane. The membrane may have a thickness of about 7 μm and pore size of about 50 nm. The nanoporous PC membrane may be deposited with a gold nano-layer 204 of about 10 nm. The deposition process may be performed by reported methods such as spin coating, dip coating, vapour deposition and the like.

Optionally or additionally, the deposition of the gold nano-layer 204 on the PC membrane 202 may be confirmed by reported analysis techniques such as atomic force microscopy (AFM). As shown in FIG. 5A, the PC membrane 202 that is successfully deposited with the gold nano-layer 204 may have a plurality of grain-like structures 502 substantially uniformly distributed on the membrane, resulting in a rough surface.

The method may then proceed to step 402 where the gold-coated membrane is modified with a coupling agent 206. In this example, the coupling agent is MCH. The coupling agent may be deposited on the gold nano-layer 204 by spin coating. For example, a solution containing a predetermined amount of MCH may be spin coated on the gold nano-layer. The sulfhydryl group of MCH may then form a gold-sulphur bond to couple with the gold nano-layer. Any excess (i.e. unreacted) MCH may be removed by washing the membrane surface with suitable solvents.

Finally, at step 403, a plurality of receptors 208 may be immobilized on the membrane 202 by reacting with the coupling agent 206. In this example, a solution containing a predetermined amount of oligo-RNA may be spin coated or dip coated on the gold-coated membrane modified with MCH 206. The oligo-RNA 208 may react with the hydroxyl group of MCH by forming a covalent bond therewith. As such, the oligo-RNAs are immobilized on the membrane. After the immobilization process, the membrane may be washed with suitable solvents such as 1×PBS (pH 7.4) followed by distilled water to remove any unreacted oligo-RNA.

Optionally or additionally, after the substance selection structure 104 is fabricated, the positive immobilization of the receptors 208 and their ability of detecting the target substance 112 may be determined by step 404. At this step, a solution of the target substance 112 that is specific to the receptors 208 may be added on the substance selection structure 104 and examined by reported techniques such as AFM. In this example, the oligo-RNA (i.e. the receptors) is specific to an antigen of gastric cancer CA72-4. A PBS solution of CA72-4 may be added on the membrane followed by being examined with AFM. As shown in FIG. 5B, a plurality of sharp peaks 504 may be observed as compared with the "bare" gold-coated PC membrane (FIG. 5A), indicating that there is a positive immobilization of the oligo-RNA and the detection of CA72-4.

Figure 6A:
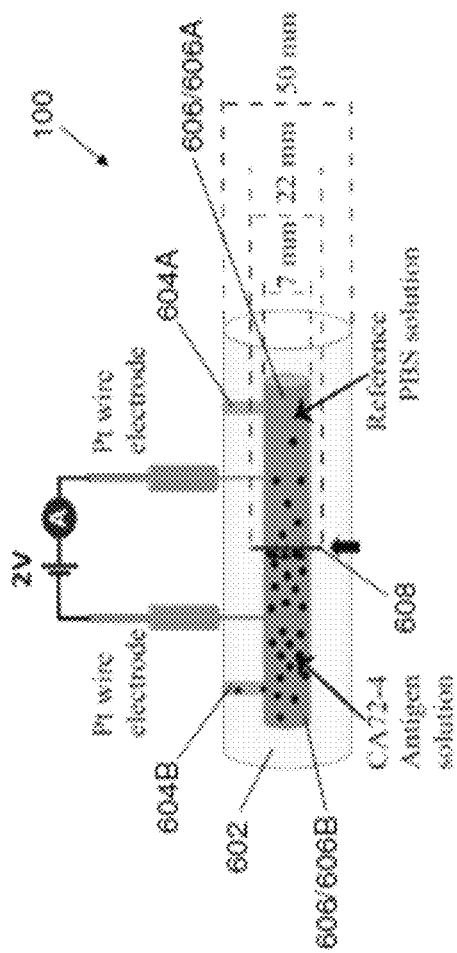
FIG. 6A is a schematic diagram showing an example operation of detecting a cancer biomarker with the electrochemical detector of FIG. 1.
Figure 6B:
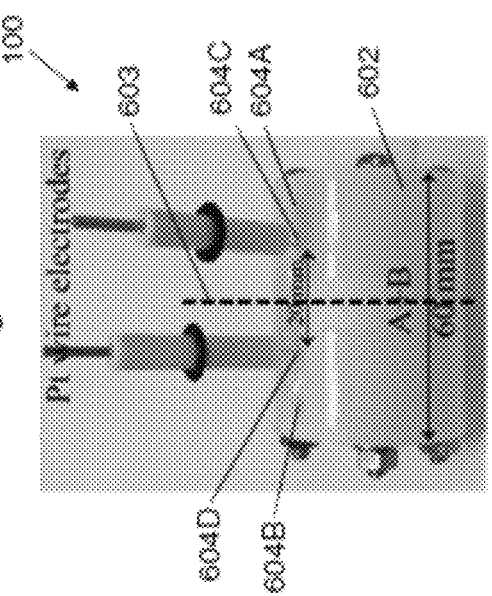
FIG. 6B is a photo showing the electrochemical detector of FIG. 6A.

With reference to FIGS. 6A to 6D, there is shown an example embodiment of detecting an antigen of gastric cancer, CA72-4 using the electrochemical detector 100. In this example, the electrochemical detector may be implemented as a cylindrical plastic solution chamber 602 (FIGS. 6A and 6B). The chamber has a length of 60 mm and a diameter of 50 mm. Such compact size of the detector may advantageously allow a user to carry the detector easily so as to carry out operations such as point-to-point diagnosis.

On the top of the chamber 602, there are provided with two pairs of pores that are symmetrically arranged with respect to the virtual axis 603. With reference to FIG. 6B, the pores 604A and 604B arranged close to each end of the chamber are inlets for directing solutions into the chamber for operation; whereas the pores (604C, 604D) close to the virtual axis 603 are where the electrodes placed for operation. Preferably, the pores 604C and 604D are spaced apart from each other by 20 mm.

Turning to the inside of the chamber, there is provided a compartment 606 for retaining solutions. In this example, the compartment has a diameter of 7 mm (FIG. 6A). The compartment 606 is separated by a chemically modified PC membrane 608, with a diameter of 22 mm, into two individual compartments 606A and 606B. Each of the individual compartments is connected to respective inlets for retaining the solution directed therefrom. In this example, the compartment 606A is fluidly connected to inlet 604A whereas the compartment 606B is fluidly connected to inlet 604B.

The PC membrane 608 is modified with a plurality of oligo-RNA for capturing the antigens of gastric cancer in the sample solution. Details of fabricating the membrane have been discussed in the method 400.

Figure 6C:
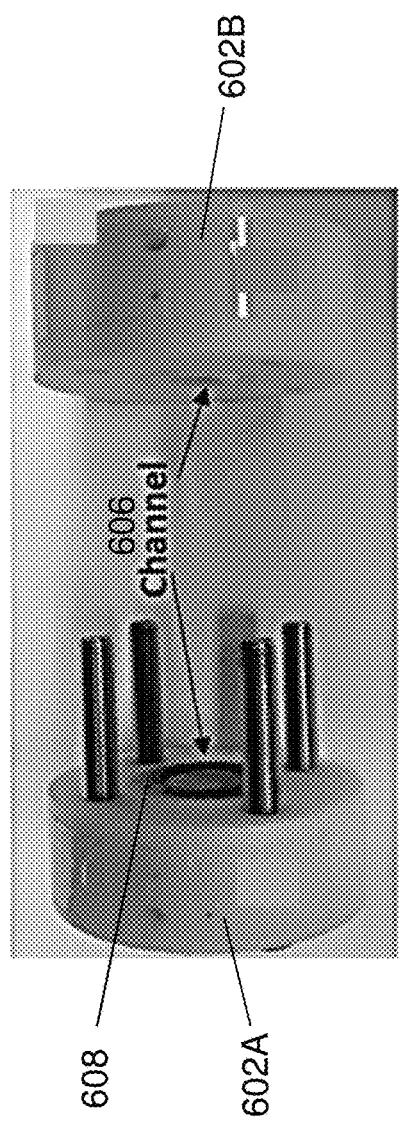
FIG. 6C is a photo showing a separable solution chamber of the electrochemical detector of FIG. 6B.

As shown in FIG. 6C, the chamber 602 is separable into two portions 602A and 602B. The two portions may be screwed to form an enclosed chamber by four screws arranged circumferentially on the chamber. Such configuration may be advantageous as the user may easily replace the PC membrane with membranes modified with other receptors for detecting other target substances. It may also be advantageous for cleaning the compartments after each measurement.

Figure 6D:
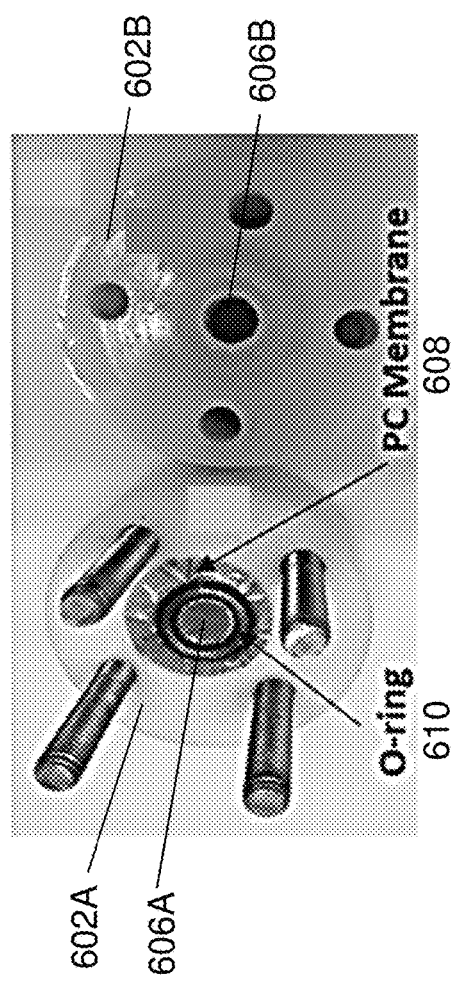
FIG. 6D is a photo showing the internal structural arrangement of the electrochemical detector of FIG. 6B.

In operation, an O-ring 610 is placed within the chamber for preventing solution leakage from any gaps between the two portions (602A, 602B). Referring to FIG. 6D, the O-ring may be placed in a recess surrounding an opening of one of the individual compartments. Preferably, the O-ring is placed in the recess surrounding the opening of the compartment 606A, which is arranged to retain a reference solution. In this way, when the two portions (602A, 602B) are screwed together, any gaps between the openings of the compartment 606A and the compartment 606B is sealed from the outside, thereby minimizing the chance of solution leakage from these compartments.

The chemically modified PC membrane 608 is placed on top of the O-ring 610, with the surface functionalized with the oligo-RNA receptors facing toward the opening of the compartment 606B. As shown in FIG. 6D, the membrane 608 may have a size that is sufficient to cover both the openings of the compartments (606A, 606B) and at least part of cross-section surface of the chamber 602. In this way, when the two portions (602A, 602B) are screwed together, the membrane 608 is sandwiched and fixed therebetween. As such, the antigens in the sample solution retained by the compartment 606B are captured by the receptors as discussed in the earlier part of this disclosure.

To perform the measurement, a PBS reference solution (1 mL) and a PBS solution containing the antigen (1 mL) are injected into the compartments 606A and 606B via the inlets 604A and 604B, respectively. A pair of platinum electrodes is inserted into the pores 604C and 604D to contact with the aforesaid sample and reference solutions. The pair of electrodes is further electrically connected to an external circuit with an ammeter so as to measure the change of current flow across the electrodes when the antigens are captured by the receptors on the membrane. The concentration of antigen in the sample solution is reflected by the magnitude of current measured.

Figure 7A:
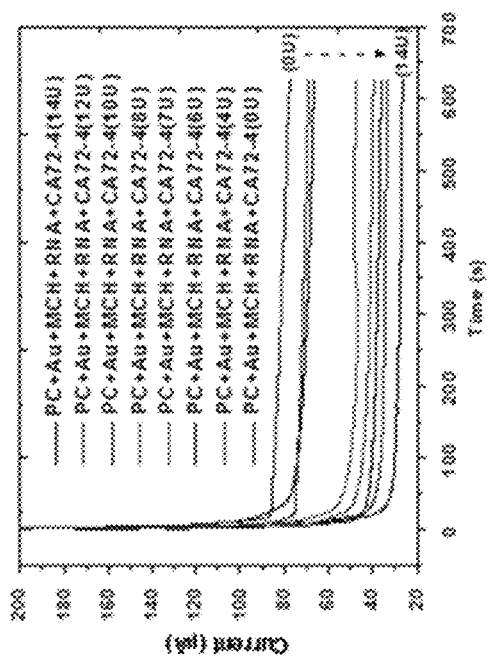
FIG. 7A is a plot of measured current against time showing sensitivity of the electrochemical detector of FIG. 6A toward different concentrations of the antigen of gastric cancer CA72-4.
Figure 7B:
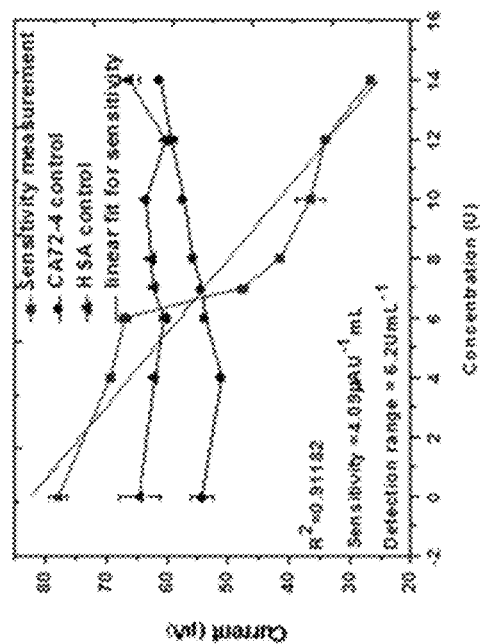
FIG. 7B is a calibration plot between the measured current values and CA72-4 detection, CA72-4 control detection, and sensitivity HSA control.

With reference to FIGS. 7A and 7B, there is shown two plots of a response of the electrochemical detector 100 in accordance with the embodiment as discussed in FIG. 6. As shown in FIG. 7A, the current across the electrodes decreases for each time the antigens are captured by the oligo-RNA receptors functionalized on the PC membrane. In particular, when the concentration of the antigen increases, the magnitude of current reduction increases accordingly, suggesting a substantially linear correlation between the antigen concentration and the current magnitude, which is in good agree with the electrophoretic transport theory.

In addition, the electrochemical detector of the present invention is highly sensitivity and selective to the target substance. As shown in FIG. 7B, the electrochemical detector 100 only showed a decrease in the measured current with respect to the increasing concentration of the target antigen (CA72-4 in this example). In sharp contrast, the measured current of the detector remained substantially unchanged toward different concentrations of CA72-4 control and HSA control, suggesting that the detector is highly selective to the target substance of interest. Furthermore, by fitting the measured current against the concentrations of the antigen as shown in FIG. 7B, the detection limit and the sensitivity of the detector are determined. In this example, the detection limit is determined to be 4 $UmL^{-1}$ whereas the sensitivity is determined to be 0.384895 $\mu AU^{-1}$ $mLcm^{-2}$. With such selectivity and sensitivity, a blood sample may be directly applied to the detector for analysis without any extra extraction processes that may cause loss of sample.

The electrochemical detector of the present invention is advantageous in that it may be implemented in portable electronic devices and hand-held sensors which may be used in domestic applications so as to provide a point-of-care service to the patients. The low-voltage (2V) operation of the electrochemical apparatus ensures chemical stability (no induced electrolysis) of analyte solutions.

Advantageously, the performance of the detection shows that the electrochemical detector has high selectivity and sensitivity for cancer biomarkers with the oligo-RNA aptamer modified membrane. In an exemplary embodiment illustrating the detection of an antigen of gastric cancer, it has been shown that the electrochemical detector containing such membrane may have a detection limit of 4 $UmL^{-1}$ and sensitivity of 0.384895 $\mu AU^{-1}$ $mLcm^{-2}$ toward the antigen.

In addition, the membrane may be easily tuned for selectively sensing the antigens of other types of cancer, or other target substances such as viruses, nanoparticles, proteins and the like, by simply fabricating different aptamers on the membrane.

Furthermore, the fabrication process is also simple and the electrochemical detector may be readily fabricated using different simple fabrication processes including low-cost fabrication methods such as printing and solution processing with low-cost materials. The fabrication of the electrochemical apparatuses may be easily scaled up. Also, the detector only requires a minimal amount of sample (i.e. 1 mL) for each measurement. In this way, the each measurement may be replicated for several times thereby minimizing the effect of measurement error.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. An electrochemical detector comprising:
 a solution chamber including a first portion and a second portion detachably connected with each other, the first and the second portions each has a compartment for containing a solution,
 a pore and an opening is provided with the first portion, the pore and the opening are opened to the compartment of the first portion; the pore and the opening are physically separated from one another;
 a pore and an opening is provided with the second portion, the pore and the opening are opened to the compartment in the second portion; the pore and the opening are physically separated from one another;
 a pair of electrodes, one being inserted into the compartment of the first portion and the other being inserted into the compartment of the second portion via the respective pores, wherein the pair of electrodes is arranged to form a conductive path when in contact with the solutions retained in the compartments; and;
 wherein a substance selection membrane comprises a porous gold deposited track-etched polycarbonate membrane having a pore size of about 50 nm, the membrane is functionalized thereon with a plurality of oligo-RNA receptors for binding with a gastric cancer antigen CA72-4 in the solution, thereby altering current flow in the conductive path; wherein the openings of both compartments are covered by the same substance selection membrane when the first and second portions are in connection with each other.

2. The electrochemical detector according to claim 1, wherein the porous gold deposited track-etched polycarbonate membrane further includes a coupling agent arranged to couple the plurality of oligo-RNA receptors with the porous gold deposited track-etched polycarbonate membrane.

3. The electrochemical detector according to claim 2, wherein the coupling agent includes a hydroxyl group forming a covalent bond with the plurality of oligo-RNA receptors.

4. The electrochemical detector according to claim 3, wherein the coupling agent further includes a sulfhydryl group arranged to couple with the porous gold deposited track-etched polycarbonate membrane.

5. The electrochemical detector according to claim 4, wherein the sulfhydryl group of the coupling agent forms a gold-sulphur bond with the porous gold deposited track-etched polycarbonate membrane.

6. The electrochemical detector according to claim 2, wherein the coupling agent is 6-mercapto-1-hexanol.

7. The electrochemical detector according to claim 1, wherein the plurality of oligo-RNA receptors forms a physical interaction with the gastric cancer antigen CA72-4.

8. The electrochemical detector according to claim 7, wherein the plurality of oligo-RNA receptors forms at least one of electrostatic interactions, hydrophobic interactions or a complementary shape with the gastric cancer antigen CA72-4.

9. The electrochemical detector according to claim 7, wherein formation of the physical interaction decreases a current flow of the conductive path.

10. The electrochemical detector according to claim 1, wherein the solution chamber is an enclosed chamber.

11. The electrochemical detector according to claim 1, wherein each of the first and the second portions includes an inlet, each connecting to the respective compartments of the chamber, for directing the solutions into the compartments.

12. The electrochemical detector according to claim 1, wherein the chamber further includes an O-ring disposed between the compartments of the first and the second portions, thereby preventing solution leakage from the respective compartments.

13. The electrochemical detector according to claim 12, wherein the O-ring is arranged on a side opposite to where the substance selection membrane interacts with the target substance.

14. The electrochemical detector according to claim 1, wherein the deposited gold has a thickness of about 10 nm.

15. The electrochemical detector according to claim 1, wherein the porous gold deposited track-etched polycarbonate membrane has a thickness of about 7 μm.

\* \* \* \* \*